United States Patent
Hill et al.

(10) Patent No.: US 6,575,176 B1
(45) Date of Patent: Jun. 10, 2003

(54) MONOFILAMENT DENTAL TAPES WITH SOFT ABRASIVE COATINGS

(75) Inventors: Ira D. Hill, Locust, NJ (US); Dale G. Brown, Wharton, TX (US)

(73) Assignee: International Tape Partners, LLC, Stafford, TX (US)

( * ) Notice: Subject to any disclaimer, the term of this patent is extended or adjusted under 35 U.S.C. 154(b) by 0 days.

(21) Appl. No.: 09/935,910

(22) Filed: Aug. 23, 2001

(51) Int. Cl.⁷ .............................................. A61C 15/00
(52) U.S. Cl. ......................................................... 132/321
(58) Field of Search ............................. 132/321, 323, 132/329

(56) References Cited

U.S. PATENT DOCUMENTS

| | | | |
|---|---|---|---|
| 3,491,776 A | * 1/1970 | Fleming | 132/321 |
| 3,699,979 A | * 10/1972 | Muhler et al. | 132/321 |
| 3,800,812 A | 4/1974 | Jaffe | 132/89 |
| 4,776,358 A | 10/1988 | Lorch | 132/321 |
| 4,795,421 A | * 1/1989 | Blasius, Jr. et al. | 604/1 |
| 4,974,615 A | 12/1990 | Doundoulakis | 132/321 |
| 5,033,488 A | 7/1991 | Curtis et al. | 132/321 |
| 5,165,913 A | * 11/1992 | Hill et al. | 132/321 |
| 5,209,251 A | 5/1993 | Curtis et al. | 132/321 |
| 5,220,932 A | 6/1993 | Blass | 132/321 |
| 5,433,226 A | 7/1995 | Burch | 132/321 |
| 5,479,952 A | 1/1996 | Zachariades et al. | 132/321 |
| 5,503,842 A | 4/1996 | Fazan et al. | 260/621 |
| 5,518,012 A | 5/1996 | Dolan et al. | 132/321 |
| RE35,439 E | 2/1997 | Rosenberger | 132/321 |
| 5,718,251 A | 2/1998 | Gray et al. | 132/321 |
| 5,755,243 A | 5/1998 | Roberts et al. | 132/321 |
| 5,760,117 A | 6/1998 | Chen | 524/270 |
| 5,765,576 A | 6/1998 | Dolan et al. | 132/321 |
| 5,787,758 A | 8/1998 | Sheldon | 74/490 |
| 5,845,652 A | 12/1998 | Tseng et al. | 132/200 |
| 5,848,600 A | 12/1998 | Bacino et al. | 132/321 |
| 5,884,639 A | 3/1999 | Chen | 132/321 |
| 5,911,228 A | 6/1999 | Curtis et al. | 132/321 |
| 5,918,609 A | 7/1999 | Tsao et al. | 132/321 |
| 5,962,572 A | 10/1999 | Chen | 524/474 |
| 5,998,431 A | 12/1999 | Tseng et al. | 514/300 |
| 6,003,525 A | 12/1999 | Katz | 132/321 |
| 6,027,592 A | 2/2000 | Tseng et al. | 156/167 |
| 6,083,208 A | 7/2000 | Modak et al. | 604/265 |
| 6,148,830 A | 11/2000 | Chen | 132/321 |
| 6,161,555 A | 12/2000 | Chen | 132/321 |

* cited by examiner

Primary Examiner—Todd E. Manahan
(74) Attorney, Agent, or Firm—Ernest V. Linek; Banner & Witcoff, Ltd.

(57) ABSTRACT

Monofilament dental tapes coated with a permanent Soft Abrasive™ coating and a saliva soluble overcoating suitable for physically disrupting and/or removing biofilms, tartar and stained pellicle.

6 Claims, No Drawings

MONOFILAMENT DENTAL TAPES WITH SOFT ABRASIVE COATINGS

BACKGROUND OF THE INVENTION

Monofilament interproximal devices are described and claimed in: U.S. Pat. Nos. Re 35,439; 3,800,812; 4,974,615; 5,760,117; 5,433,226; 5,479,952; 5,503,842; 5,755,243; 5,845,652; 5,884,639; 5,918,609; 5,962,572; 5,998,431; 6,003,525; 6,083,208; 6,148,830; 6,161,555; and 6,027,592, the disclosures of which are hereby incorporated herein by reference. These dental tapes generally have serious shortcomings in gentleness, in delivering coatings during flossing and in being handled easily and conveniently during flossing Polytetrafluoroethylene (PTFE) based interproximal devices are described in: U.S. Pat. Nos. 5,209,251; 5,033,488; 5,518,012; 5,911,228; 5,220,932; 4,776,358; 5,718,251; 5,848,600; 5,787,758; and 5,765,576. To date, no commercial versions of these tapes have been coated effectively and cannot be used to deliver active ingredients, interproximally and subgingivally during flossing. Handling during flossing is difficult. Most have to provide a consumer acceptable edge. Many are plagued with serious dimensional inconsistency problems, as well.

Several Patent Applications have been filed on monofilament dental tapes with coatings comprising from between about 20% by weight and about 120% by weight of the monofilament tape. These are described in copending U.S. Provisional Patent Application Serial Nos. 60/227,433 and 60/227,255, filed Aug. 23, 2000 and Serial No. 60/263,220, filed Jan. 22, 2001, all of which are hereby incorporated by reference.

SUMMARY OF THE INVENTION

The present invention is directed to coated monofilament tapes with improved abrasive properties having a precoating that permanently holds abrasives to the tape during flossing, while simultaneously releasing a second saliva soluble overcoating containing various cleaning, mouth conditioning and therapeutic substances.

The permanent abrasive coating is described as a "Soft Abrasive™" that is effective during flossing in gently physically disrupting and/or removing: supragingival plaque and tartar, plaque and tartar at the gingival margin, interproximal plaque and tartar, subgingival plaque (biofilm), and supragingival and interproximal stained pellicle, etc.

Accordingly, one embodiment of the present invention is monofilament dental tapes coated with a Soft Abrasive™ permanent coating and overcoated with a saliva soluble coating suitable for physically removing biofilms, tartar and stained pellicle from interproximal, subgingival and gingival margin areas of teeth.

Preferably, the Soft Abrasive™ used with these monofilament dental tapes comprises a permanent coating that contains a permanent adhesive selected from the group consisting of polyvinyl, alcohol-based, epoxy-based, solvent-based, radiant-cured, methacrylate-based, polyurethane-based, natural and other synthetic-based adhesives and combinations thereof. More preferably, the Soft Abrasive™ permanent coating contains an abrasive selected from the group consisting of tricresylphosphate, dicalcium phosphate, pumice, aluminum silicate, silica, glass beads, titanium oxide, rice flour, quartz, novaculite, silicon carbide, alumina zirconia, alumina, polishing alumina, calcined aluminum oxide, calcium oxide, silicon and zirconium oxide and combinations thereof.

Another embodiment of the present invention comprises a method for removing tartar, biofilms and stained pellicle. The method comprises flossing regularly (i.e., at least once daily) with a monofilament dental tape coated with a Soft Abrasive™ permanent coating and overcoated with a saliva soluble coating suitable for physically removing biofilms, tartar and stained pellicle from interproximal, subgingival and gingival margin areas of teeth.

Another preferred embodiment of the present invention comprises a method for manufacturing monofilament dental tapes coated with a permanent Soft Abrasive™ and overcoated with a saliva soluble coating. The preferred manufacturing method comprises the steps of:

(a) precoating said tape with a permanent adhesive at from between about 1% and about 30% by weight of said monofilament tape;

(b) adding an abrasive at from between about 0.25% and about 20% by weight of the monofilament tape;

(c) curing said adhesive/abrasive coating; and (d) coating said treated tape with a saliva soluble coating at from between about 30 mg/yd and about 70 mg/yd.

DETAILED DESCRIPTION OF THE PREFERRED EMBODIMENTS

In order to improve biofilm disruption and/or removal with coated monofilament dental tapes, it has been found that these tapes require more abrasive action than can be achieved with the various saliva soluble coatings containing various abrasives at various levels. Eventually, these saliva soluble coatings, with their high abrasive contents, are "worked" out of those interproximal, subgingival and gingival margin areas, where they have been delivered during flossing by saliva and crevicular fluid flow, in combination with the sawing action that takes place during flossing. All of the foregoing tend to dilute-out the abrasives released during flossing and to minimize their tartar, biofilm and stained pellicle physical disruption and/or removal capabilities.

Therefore, one preferred embodiment of the present invention is a method for the improved removal of tartar, biofilm and stained pellicle, in which the method comprises the physical removal and/or disruption of these materials by cleaning with monofilament dental tapes having improved physical abrasive properties.

Another preferred embodiment of the invention comprises the coated monofilament dental tapes described herein, which include the gentle permanent abrasive properties described.

Still another preferred embodiment of the invention is a process for producing saliva soluble coated monofilament dental tapes with an insoluble permanent abrasive coating that gently removes and/or disrupts tartar, biofilms and stained pellicle.

Yet another preferred embodiment of the invention is an improved method for physically removing and/or disrupting tartar, biofilm and stained pellicle using coated monofilament dental tapes with improved abrasive action For the purposes of the invention, various monofilament dental tapes including PTFE, elastomeric, homopolymer and bicomponent dental tapes are precoated with a permanent adhesive selected from a wide range of adhesives including polyvinyl alcohol based adhesives, polyurethane adhesives, epoxy adhesives, ultraviolet cured adhesives, polymethacrylate based adhesives, etc.

Various abrasives are added to the adhesive prior to the adhesive curing in a manner that allows at least a portion of the adhesive surface to be available for imparting abrasive action to the monofilament tape during flossing. The "sand paper" effect of these various adhesive/abrasive combinations produces a gentle "Soft Abrasive™" action when combined with the saliva soluble coating substances in the overcoating applied to the permanent adhesive coating for release from the tape during flossing.

Suitable adhesives for the permanent Soft Abrasive™ coatings on monofilament dental tapes of the present invention include:

- polyvinyl alcohol (PVA) polymer based adhesives that can be fully hydrolyzed, partially hydrolyzed and copolymerized under the trademark Elvanol®, including Elvanol® Grades: 50-42, 51-05, 52-22, 70-06, 71-30, 75-15, 85-30, 85-82, 90-50, T-25 and T-25 LR,
- solvent based adhesives,
- radiant cured adhesives including UV light and electron beam (EB) cured adhesive,
- epoxy based adhesives,
- methacrylate based adhesive,
- polyurethane based adhesives, and
- other natural and synthetic adhesive substances that will adhere to those monofilament substrates as described in Tables 1 through 4 below.

The adhesives can comprise from between about 1% and about 30% by weight of the monofilament tape.

Suitable abrasives for use in the monofilament dental tapes of the present invention, which are designated by the trademark "Soft Abrasive™," include tricresylphosphate (TCP), dicalcium phosphate (DCP), pumice, aluminum silicate, silica, glass beads, titanium oxide, rice flour, quartz, novaculite, silicon carbide, alumina zirconia, alumina, polishing alumina, calcined aluminum oxide, calcium oxide, silicon and zirconium oxide; all of the foregoing at various crystal forms, particle shapes, including platy and hexagonal; various hardness including Rockwell 48–50c at various sieve analysis ranging from U.S. sieve #6 to #40; various specific gravity ranges including 2.65 gm/cc, 3.20 gm/cc, 4.3 gm/cc, 3.6 to 3.9 gm/cc.

These abrasives are added to adhesive precoated monofilament tape at between about 0.25% and about 20% by weight of the monofilament tape. A preferred method of adding the abrasive to the adhesive precoated tape is by means of a dusting process where the tape is passed through a chamber charged with abrasive particles in the air, wherein the abrasive particles coat the precured adhesive coated tape as it passes through the dusting chamber.

Some of these abrasives are commercially available from AGSCO Corp. Wheeling, Ill.

Suitable monofilament tapes such as described in Tables 1 through 4 below can be precoated with Soft Abrasives™ including adhesive/abrasive combinations such as described above to produce Soft Abrasive™ tapes wherein the adhesive/abrasive combination comprises from between about 1% and about 50% by weight of said monofilament tapes. These Soft Abrasive™ tapes are then overcoated with saliva soluble coatings such as described in Table 5 to produce Soft Abrasive™ coated monofilament tapes.

TABLE 1

TAPE COMPOSITION

| Ex. No. | Thermoplastic Elastomer Type | Manufacturer | Trade name | Grade | Silicone Process Aid (%) | TiO$_2$ (%) | Secondary Polymer added Type (%) | Other Add'n Type (%) |
|---|---|---|---|---|---|---|---|---|
| 2 | PEBA polyester amide | Atofina | PEBAX | 55/33 | 3.5 | 1.8 | PP-4.7 | — |
| 3 | PEBA polyester amide | " | " | " | 3.5 | 1.8 | PP-4.7 Adflex-5 | — |
| 4 | PEBA polyester amide | " | " | " | 3.5 | 1.8 | PP-9.7 | — |
| 5 | PEBA polyester amide | Atofina | PEBAX | 63/33 | 0 | 0 | 0 | — |
| 6 | PEBA polyester amide | " | " | " | 0 | 1.8 | PP-1.2 | — |
| 7 | PEBA polyester amide | " | " | " | 3.5 | 1.8 | PP-4.7 | — |
| 8 | PEBA polyester amide | " | " | " | 3.5 | 1.8 | PP-4.7 Adflex-5 | — |
| 9 | PEBA polyester amide | " | " | " | 3.5 | 1.8 | PP-9.7 | — |
| 10 | PEBA polyester amide | " | " | " | 3.5 | 1.8 | PP-4.7 Nylon 11-5 | — |
| 11 | TPE polyether ester | Dupont | Hytrel | 6359FG | 2.3 | 1.0 | 0 | Ca Stearate 0.1 |
| 12 | TPE polyether ester | " | " | " | 3.5 | 1.8 | PP-4.7 | Ca Stearate 0.1 |
| 13 | TPE-E polyether ester | DSM | Arnitel | PM581 | 0 | 0 | 0 | — |
| 14 | TPE-E polyether ester | " | " | " | 0 | 1.8 | PP-1.2 | — |
| 15 | TPE-E polyether ester | " | " | " | 3 | 0 | PBT-5 | — |
| 16 | TPE-E polyether ester | " | " | " | 0 | 0 | PBT-5 | — |
| 17 | TPE-E polyether ester | " | " | " | 0 | 1.8 | PP-1.2 PBT-5 | — |

TABLE 1-continued

| | TAPE COMPOSITION | | | | | | | | | | | |
|---|---|---|---|---|---|---|---|---|---|---|---|---|
| | PROCESSING | | | PROPERTIES | | | | | | UTILITY FACTORS | | |
| | CONDITIONS | | | Break | Elonga- | | | | | Gentle- | Tape | |
| | Melt | Draw | | Strength | tion to | Elastic | | DIMENSIONS | | ness | Flex | Hard- |
| Ex. No. | Temp °C. | Temp °C. | Draw Ratio | in Newtons | Break (%) | Limit (%) | Decitex | Width (mm) | Thick (mm) | Percep- tion | Twist Index | ness Shore D |
| 2 | 260 | 130 | 6.8:1 | 30 | 26 | 0 | 750 | 1.30 | 0.063 | 6 | 4 | 37 |
| 3 | 260 | 130 | 6.5:1 | 27 | 18 | 0 | 760 | 1.30 | 0.063 | 6 | 4 | 37 |
| 4 | 260 | 130 | 6.8:1 | 26 | 19 | 0 | 760 | 1.30 | 0.063 | 6 | 4 | 37 |
| 5 | 260 | 135 | 6:1 | 30 | 15 | 0 | 805 | 1.44 | 0.065 | 5.5 | 4 | 36 |
| 6 | 260 | 135 | 6.3:1 | 32.36 | 13 | 0 | 800 | 1.41 | 0.067 | 5.5 | 4 | 36 |
| 7 | 260 | 135 | 6.2:1 | 33.47 | 17 | 0 | 860 | 1.36 | 0.066 | 5.5 | 4 | 36 |
| 8 | 260 | 135 | 6.2:1 | 25.94 | 14 | 0 | 810 | 1.32 | 0.078 | 5.5 | 4 | 36 |
| 9 | 260 | 135 | 6.2:1 | 29.46 | 14 | 0 | 780 | 1.34 | 0.069 | 5.5 | 4 | 36 |
| 10 | 260 | 135 | 6.2:1 | 30.63 | 13 | 0 | 810 | 1.30 | 0.065 | 5.5 | 4 | 36 |
| 11 | 225 | 130 | 5:1 | 20 | 20 | 15 | 1400 | 1.70 | 0.070 | 7 | 3 | 33 |
| 12 | 225 | 140 | 5.7:1 | 24 | 14 | 10 | 1230 | 1.70 | 0.070 | 7 | 3 | 33 |
| 13 | 235 | 140 | 4.3:1 | 18 | 13 | 10 | 1500 | 1.63 | 0.084 | 7 | 3 | 33 |
| 14 | 240 | 115 | 4.3:1 | 19 | 14 | 5 | 1634 | 1.64 | 0.085 | 7 | 3 | 33 |
| 15 | 235 | 140 | 4.3:1 | 19 | 10 | 3 | 1580 | 1.68 | 0.079 | 7 | 3 | 33 |
| 16 | 235 | 140 | 4.3:1 | 18 | 12 | 2 | 1500 | 1.70 | 0.086 | 7 | 3 | 33 |
| 17 | 235 | 140 | 4.3:1 | 21 | 15 | 4 | 1575 | 1.77 | 0.083 | 7 | 3 | 33 |

TABLE 2

| | TAPE COMPOSITION | | | | | | | |
|---|---|---|---|---|---|---|---|---|
| Ex. No. | Thermoplastic Elastomer Type | Manufacturer | Trade- name | Grade | Silicone Process Aid (%) | TiO$_2$ (%) | Secondary Polymer added Type (%) | Other Add'n Type (%) |
| 18 | TPE-E polyether ester | DSM | Arnitel | EM550 | 0 | 0 | 0 | — |
| 19 | TPE-E polyether ester | " | " | " | 0 | 1.8 | PP-1.2 | — |
| 20 | TPE-E polyether ester | " | " | " | 0 | 1.8 | PP-6.2 | — |
| 21 | TPE-E polyether ester | " | " | " | 0 | 0 | PBT-5 | — |
| 22 | TPE-P polyether ester | OSM | Arnitel | EM630 | 0 | 0 | 0 | — |
| 23 | TPE-P polyether ester | " | " | " | 0 | 1.8 | PP-1.2 | — |
| 24 | TPE-P polyether ester | " | " | " | 0 | 1.8 | PP-1.2 Adflex-5 | — |
| 25 | TPE-P polyether ester | " | " | " | 0 | 1.8 | PP-6.2 | — |
| 26 | TPE-P polyether ester | " | " | " | 0 | 0 | PBT-5 | — |
| 27 | TPE-P polyester ester | DSM | Arnitel | UM552 | 0 | 0 | 0 | — |
| 28 | TPE-P polyester ester | " | " | " | 0 | 0 | 0 | Ca Stearate 0.1 |
| 29 | TPE-P polyester ester | " | " | " | 0 | 1.8 | PP-1.2 | — |
| 30 | TPE-P polyester ester | " | " | " | 0 | 0 | Adflex-5 | — |
| 31 | TPE-P polyester ester | " | " | " | 0 | 1.5 | PP-1.2 PBT-5 | Ca Stearate 0.1 |
| 32 | TPE-P polyester ester | " | " | " | 0 | 0 | PBT-5 | Ca Stearate 0.1 |
| 33 | EPDM TPV | Monteil | Adflex | Q100F | 0 | 0 | PP-20 | — |
| 34 | EPDM TPV | " | " | " | 3.5 | 1.8 | PP-24.7 | — |
| 35 | EPDM TPV | " | " | " | 7 | 3 | PP-30 | — |
| 36 | EPDM TPV | " | " | " | 7 | 3 | PP-34.7 | — |
| 37 | EPDM | " | " | " | 7 | 3 | PP-40 | — |

TABLE 2-continued

TAPE COMPOSITION

| | TPV PROCESSING CONDITIONS | | | PROPERTIES | | | DIMENSIONS | | | UTILITY FACTORS | | |
|---|---|---|---|---|---|---|---|---|---|---|---|---|
| Ex. No. | Melt Temp °C. | Draw Temp °C. | Draw Ratio | Break Strength in Newtons | Elongation to Break (%) | Elastic Limit (%) | Decitex | Width (mm) | Thickness (mm) | Gentleness Perception | Tape Flex Twist Index | Hardness Shore D |
| 18 | 240 | 140 | 4.3:1 | 23 | 25 | 7 | 1800 | 1.95 | 0.096 | 7 | 3 | 33 |
| 19 | 240 | 115 | 6:1 | 27 | 11 | 5 | 1050 | 1.47 | 0.071 | 7 | 3 | 33 |
| 20 | 240 | 140 | 5.6:1 | 26 | 17 | 5 | 1216 | 1.45 | 0.071 | 7 | 3 | 33 |
| 21 | 240 | 145 | 5.9:1 | 28 | 145 | 5 | 1220 | 1.55 | 0.074 | 7 | 3 | 33 |
| 22 | 235 | 150 | 4.5:1 | 18 | 12 | 4 | 1090 | 1.44 | 0.067 | 7 | 3 | 33 |
| 23 | 235 | 150 | 4.7:1 | 17 | 11 | 4 | 1130 | 1.50 | 0.068 | 7 | 3 | 33 |
| 24 | 235 | 150 | 4.6:1 | 18 | 10 | 7 | 961 | 1.35 | 0.065 | 7 | 3 | 33 |
| 25 | 235 | 150 | 4.6:1 | 14 | 30 | 10 | 965 | 1.24 | 0.073 | 7 | 3 | 33 |
| 26 | 235 | 150 | 4.6:1 | 20 | 12 | 5 | 1018 | 1.39 | 0.069 | 7 | 3 | 33 |
| 27 | 240 | 150 | 6.6:1 | 32 | 12 | 8 | 1300 | 1.49 | 0.070 | 7.5 | 3.5 | 31 |
| 28 | 230 | 150 | 5.6:1 | 26 | 15 | 8 | 1090 | 1.40 | 0.070 | 7.5 | 3.5 | 31 |
| 29 | 240 | 150 | 6.3:1 | 29 | 16 | 8 | 1150 | 1.46 | 0.070 | 7.5 | 3.5 | 31 |
| 30 | 230 | 140 | 5.6:1 | 30 | 16 | 10 | 1233 | 1.48 | 0.069 | 7.5 | 3.5 | 31 |
| 31 | 230 | 145 | 5.7:1 | 22 | 19 | 10 | 1108 | 1.53 | 0.067 | 7.5 | 3.5 | 31 |
| 32 | 230 | 245 | 5.3:1 | 24 | 14 | 8 | 1143 | 1.48 | 0.064 | 7.5 | 3.5 | 31 |
| 33 | 240 | 130 | 4.5:1 | 26 | 20 | 0 | 910 | 1.60 | 0.064 | 5.5 | NT | NT |
| 34 | 240 | 130 | 4.5:1 | 25 | 24 | 0 | 940 | 1.59 | 0.064 | 5.5 | NT | NT |
| 35 | 240 | 130 | 4.7:1 | 28 | 20 | 0 | 870 | 1.58 | 0.064 | 5.5 | NT | NT |
| 36 | 240 | 130 | 4.7:1 | 27 | 23 | 0 | 880 | 1.58 | 0.060 | 5.5 | NT | NT |
| 37 | 240 | 130 | 4.7:1 | 35 | 18 | 0 | 720 | 1.44 | 0.063 | 5 | NT | NT |

TABLE 3

TAPE COMPOSITION

| Ex. No. | Thermoplastic Elastomer Type | Manufacturer | Tradename | Grade | Silicone Process Aid (%) | TiO₂ (%) | Secondary Polymer added Type (%) | Other Add'n Type (%) |
|---|---|---|---|---|---|---|---|---|
| 38 | PEBA polyester amide | Atofina | PEBAX | 55133 | 0 | 1.8 | PP-1.2 | — |
| 39 | PEBA polyester amide | " | " | " | 3.5 | 1.8 | PP-4.7 EMA-3 | — |
| 40 | PEBA polyester amide | " | " | " | 3.5 | 1.8 | PP-4.7 | — |
| 41 | PEBA | Atofina | PEBAX | 63/33 | 3.5 | 1.8 | PP-4.7 EMA-3 | — |
| 42 | " | " | " | " | 0 | 0 | Nylon 11-5 | PDVF -3 |
| 43 | TPE-E polyether ester | DSM | Arnitel | PM581 | 3 | 0 | 0 | — |
| 44 | TPE-E polyether ester | DSM | Amitel | EM550 | 3 | 0 | 0 | — |
| 45 | TPE-E polyether ester | " | " | " | 3 | 1.8 | PP-1.2 EMA-3 | — |
| 46 | TPE-E polyether ester | DSM | Arnitel | UM552 | 3 | 1.8 | PP-1.2 | — |

| | PROCESSING CONDITIONS | | | PROPERTIES | | | DIMENSIONS | | | UTILITY FACTORS | | |
|---|---|---|---|---|---|---|---|---|---|---|---|---|
| Ex. No. | Melt Temp °C. | Draw Temp °C. | Draw Ratio | Break Strength in Newtons | Elongation to Break (%) | Elastic Limit (%) | Decitex | Width (mm) | Thickness (mm) | Gentleness Perception | Tape Flex Twist Index | Hardness Shore D |
| 38 | 260 | 130 | 6.8:1 | 28 | 24 | 0 | 775 | 1.30 | 0.063 | 6 | 4 | 37 |
| 39 | 260 | 130 | 7:1 | 28 | 30 | 3 | 750 | 1.30 | 0.063 | 8 | 4 | 37 |
| 40 | 260 | 130 | 6.8:1 | 29 | 24 | 0 | 800 | 1.35 | 0.070 | 6 | 4 | 37 |
| 41 | 260 | 135 | 6.5:1 | 31 | 20 | 3 | 800 | 1.40 | 0.065 | 5.5 | 4 | 36 |
| 42 | 260 | 135 | 6.2:1 | 28 | 14 | 0 | 800 | 1.30 | 0.065 | 5.5 | 4 | 36 |

TABLE 3-continued

| | | | | | TAPE COMPOSITION | | | | | | |
|---|---|---|---|---|---|---|---|---|---|---|---|
| 43 | 235 | 140 | 5:1 | 22 | 16 | 7 | 1400 | 1.60 | 0.079 | 7 | 3 | 33 |
| 44 | 240 | 140 | 6:1 | 25 | 20 | 7 | 800 | 1.30 | 0.060 | 7 | 3 | 33 |
| 45 | 240 | 140 | 6:1 | 27 | 15 | 5 | 850 | 1.35 | 0.065 | 7 | 3 | 33 |
| 46 | 240 | 150 | 6:1 | 27 | 17 | 10 | 1100 | 1.47 | 0.069 | 7.5 | 3 | 33 |

TABLE 4

| | | | | | TAPE COMPOSITION | | | |
|---|---|---|---|---|---|---|---|---|
| Ex. No. | Thermoplastic Elastomer Type | Manufacturer | Trade-name | Grade | Silicone Process Aid (%) | TiO$_2$ (%) | Secondary Polymer added Type (%) | Other Add'n Type (%) |
| 47 | Styrenics SEBS | Alphagary | Evo-prene | G978 | 0 | 1.8 | PP-1.2 | — |
| 48 | Styrenics SEBS | " | Evo-prene | " | 3 | 1.8 | PP-1.2 | — |
| 49 | Styrenics SEBS | " | Evo-prene | " | 0 | 1.8 | PP-1.2 EMA-3 | — |
| 50 | Styrenics SEBS | " | Evo-prene | " | 3.5 | 1.8 | PP-9.7 | — |
| 51 | Styrenics S PP-9.7 90AEN | " | Evo-thane | " | 3.5 | 1.8 | PP-9.7 | — |
| 56 | TPV | DSM | Sarlink | 4149D | 0 | 1.8 | PP-1.2 | — |
| 57 | " | " | " | " | 3 | 1.8 | PP-1.2 | — |
| 58 | " | " | " | " | 0 | 1.8 | PP-1.2 EMA-3 | — |
| 59 | " | " | " | " | 3 | 1.8 | PP-6.2 | — |

| | PROCESSING CONDITIONS | | PROPERTIES | | | | | | UTILITY FACTORS | | |
|---|---|---|---|---|---|---|---|---|---|---|---|
| Ex. No. | Melt Temp °C. | Draw Temp °C. | Draw Ratio | Break Strength in Newtons | Elongation to Break (%) | Elastic Limit (%) | Decitex | Width (mm) | Thickness (mm) | Gentleness Perception | Tape Flex Twist Index | Hardness Shore D |
| 47 | 200 | 100 | 7:1 | 19 | 30 | 10 | 1100 | 1.30 | 0.060 | 6 | 4 | 37 |
| 48 | 200 | 100 | 7:1 | 20 | 35 | 12 | 1100 | 1.30 | 0.060 | 6 | 4 | 37 |
| 49 | 200 | 100 | 7.2:1 | 17 | 32 | 12 | 1100 | 1.30 | 0.060 | 6 | 4 | 37 |
| 50 | 200 | 100 | 7:1 | 14 | 20 | 7 | 1100 | 1.30 | 0.060 | 8 | 4 | 37 |
| 51 | 200 | 100 | 7:1 | 22 | 28 | 8 | 1100 | 1.30 | 0.060 | 6 | 4 | 37 |
| 52 | 230 | 120 | 7:1 | 32 | 15 | 5 | 1200 | 1.40 | 0.068 | 7 | 3 | 33 |
| 53 | 230 | 120 | 6:1 | 30 | 17 | 6 | 1200 | 1.40 | 0.068 | 7 | 3 | 33 |
| 54 | 230 | 120 | 6:1 | 26 | 16 | 6 | 1200 | 1.40 | 0.068 | 7 | 3 | 33 |
| 55 | 230 | 120 | 5:1 | 22 | 10 | 2 | 1300 | 1.45 | 0.070 | 7 | 3 | 33 |
| 56 | 220 | 105 | 4.5:1 | 20 | 20 | 5 | 1400 | 1.45 | 0.072 | 6 | 4 | 37 |
| 57 | 220 | 105 | 5:1 | 22 | 35 | 7 | 1300 | 1.40 | 0.070 | 6 | 4 | 37 |
| 58 | 220 | 105 | 4.8:1 | 19 | 20 | 5 | 1350 | 1.48 | 0.075 | 6 | 4 | 37 |
| 59 | 220 | 105 | 4.2:1 | 15 | 20 | 5 | 1450 | 1.48 | 0.075 | 6 | 4 | 37 |

Saliva soluble coatings for monofilament tapes to be bobbin wound according to the present invention are described in Table 5 below. In the Table, the term "Ultramulsion 10–2.5" is defined as an emulsion of polydimethylsoloxane (PDMS) at 2.5 million cs in a nonionic surfactant Poloxamer 407, where the PDMS is at 10% by weight of the total emulsion.

TABLE 5

| EXAMPLE | 60 | 61 | 62 | 63 | 64 | 65 | 66 | 67 | 68 | 69 | 70 | 71 | 72 | 73 | 74 | 75 | 76 | 77 |
|---|---|---|---|---|---|---|---|---|---|---|---|---|---|---|---|---|---|---|
| Ingredient | | | | | | | | | | | | | | | | | | |
| Ultramulsion 10–2.5* | 57.1 | 54.8 | 52.3 | 50.8 | 50.8 | 50.8 | 58.8 | 60.8 | | 60.1 | 55.1 | 51.1 | 60.1 | | 61.1 | 61.1 | 53.1 | 57.1 |
| POLOXAMER 407 | | | | | | | | | 60.1 | | | | | 60.1 | | | | |
| Emsorb 2726 | 12.5 | 7.5 | 12.5 | 9 | 5 | 3 | 3 | 0 | 3 | 3 | 3 | 3 | 3 | 3 | 4 | 3 | 3 | 3 |

TABLE 5-continued

| EXAMPLE | 60 | 61 | 62 | 63 | 64 | 65 | 66 | 67 | 68 | 69 | 70 | 71 | 72 | 73 | 74 | 75 | 76 | 77 |
|---|---|---|---|---|---|---|---|---|---|---|---|---|---|---|---|---|---|---|
| Stearyl Alcohol | 9.2 | 10.5 | 8 | 7 | 11 | 13 | 15 | 16 | 15 | 15 | 15 | 15 | 15 | 15 | 10 | 8 | 15 | 15 |
| Insoluble Saccharin | 1.8 | 1.8 | 1.8 | 1.8 | 1.8 | 1.8 | 1.8 | 1.8 | 1.8 | 1.8 | 1.8 | 1.8 | 1.8 | 1.8 | 1.8 | 1.8 | 1.8 | 1.8 |
| Propyl gallate | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| Spicemint Flavor | 4 | 4 | 4 | 4 | 4 | 4 | 4 | 4 | 5 | 5 | 5 | 5 | 5 | 5 | 5 | 5 | 5 | 5 |
| Vanilla Mint Flavor | 4 | 4 | 4 | 4 | 4 | 4 | 4 | 4 | 5 | 5 | 5 | 5 | 5 | 5 | 5 | 5 | 5 | 5 |
| Tetrasodium-pyrophosphate | 8 | 14 | 14 | 10 | 10 | 10 | 10 | 10 | 10 | | 10 | 14 | 4 | | 6 | 6 | 10 | 6 |
| dicalcium phosphate | | | | | | | | | | 10 | | | 6 | 10 | | | | |
| Microcrystalline Wax ML 445 | | | 10 | 10 | 10 | 0 | 0 | 0 | 0 | 5 | 5 | | | 0 | 7 | 10 | 7 | 7 |
| Triclosan | 3.3 | 3.3 | 3.3 | 3.3 | 3.3 | 3.3 | 3.3 | 3.3 | | | | | | | | | | |
| Observation | | | | | | | | | | | | | | | | | | |
| Need heat to wind | y | | n | y | y | n | Y | Y | y | y | y | y | y | y | y | y | y | y |
| Bobbin tack (1 = poor, 5 = good) | 1 | | 5 | 5 | 3 | 4 | | 4 | 3 | 2 | 4 | 4 | 3 | 3 | 4 | 3 | 4 | 4 |
| Flake resistance | | | | | | | | | | | | | | | | | | |
| Feels sticky (1 = no, 5 = very) | | | 5 | 4 | 4 | 2 | 1 | 2 | 2 | 3 | 3 | 3 | 1 | 4 | 3 | 4 | 4 |
| Load of tw0 samples | 29/19 | na | na | 43/50 | 28/11 | 53/39 | 58/43 | 33/20 | 51/40 | 33 | 46/53 | 40/39 | 38/38 | 50/37 | 48 | 45 | 38/39 | 43/39 |

ADDITIONAL EXAMPLES

In the following example, the monofilament the tape was Fibaclean™ from the Perident Company with a thickness of 0.0025 inches and a width of 0.050 in. The heated rollers were set with a gap of 0.002" to 0.0002", temperatures ranged from 110–150° C. depending on the melt-emulsion viscosity requirements.

Example 78

A series of chemotherapeutic tapes were precoated with PVA adhesives of the Elvanol® series described above at between about 1% and 5% by weight of the monofilament tape. A series of different adhesives were added to the adhesive coated tapes prior to curing of the adhesive on each tape. The abrasives were added to the precured adhesive by passing the precoated tape through an abrasive charged chamber where the abrasive particles are maintained in the air of the chamber by a supplemental air charging means. Various Soft Abrasive™ tapes for the purposes of the present invention with abrasives including pumice, aluminum silicate and silicon carbide present on the tape at from between about 0.5% by weight and about 5% by weight of the monofilament tape are prepared with an overcoating of a saliva soluble substance as described below.

Chlorhexidine Chemotherapeutic Monofilament Tape

A saliva soluble overcoating was added to these abrasive containing tapes at about 52 g/m. This coating comprised:

| Melt-Emulsion Ingredients | % w/w | Load mg/yd | Final Thickness |
|---|---|---|---|
| Poloxamer F-127 | 56.52 | | |
| 2.5 MM cs PDMS[(1)] | 6.28 | | |
| PEG 1450 | 7.0 | | |
| Mic. Wax ML 445 | 22.4 | 53.2 | 0.005 in. |
| Saccharin, insol | 1.8 | | |
| Flavor | 5.4 | | |
| chlorhexidine base | 0.6 | | |

[(1)]PDMS = polydimethylsiloxane at 2,500,00 cs viscosity combined with the Poloxamer F-127 in the form of an Ultramulsion as described in various Hill patents.

The various Soft Abrasive™ tapes produced as described above can be packaged in single dose packages for dispensing as an Rx product under prescription. Each of these single dose Soft Abrasive™ chlorhexidine tapes releases about 0.6% by weight CHX during flossing and simultaneously removes CHX-stained pellicle from previous treatments, thereby controlling the level of CHX-stained pellicle associated with this treatment. This reduced level of pellicle staining is a primary attribute of this CHX treatment that promotes compliance.

Example 79

Prophy Flosses:

A series of monofilament dental tapes as described in Examples 2 through 59 are precoated with "prophy paste"-type abrasives including pumice, silica, DCP, alumina silicate, and silicon carbide, secured to the tape using a series of radiant curable adhesives. These various abrasive substances are maintained in an abrasive charged chamber through which the adhesive coated tape is passed. The tapes are radiant cured after addition of the adhesive. These "prophy" adhesives are present on the various tapes at from between about 0.25% and about 5% by weight of the monofilament tape. All the tapes are overcoated with one of the saliva soluble coatings as described in Examples 60 through 77.

The saliva soluble coatings are added to the adhesives containing tapes at between about 30 and about 70 mg/yd.

The resultant tapes are used exclusively by oral care professionals and particularly oral hygienists in their prophylaxis procedures.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. Monofilament dental tapes coated with a permanent abrasive coating and overcoated with a saliva soluble coating suitable for physically removing biofllms, tartar and stained pellicle from interproximal, subgingival and gingival margin areas of teeth.

2. Monofilament dental tapes according to claim 1, wherein said permanent abrasive coating contains a permanent adhesive selected from the group consisting of polyvinyl alcohol-based, epoxy-based, solvent-based, radiant-cured, methacrylate-based, polyurethane-based, natural and other synthetic-based adhesives and combinations thereof.

3. Monofilament dental tapes according to claim 1, wherein said permanent abrasive coating contains an abrasive selected from the group consisting of tricresylphosphate, dicalcium phosphate, pumice, aluminum silicate, silica, glass beads, titanium oxide, rice flour, quartz, novaculite, silicon carbide, alumina zirconia, alumina, polishing alumina, calcined aluminum oxide, calcium oxide, silicon and zirconium oxide and combinations thereof.

4. A method for removing tartar, biofilms and stained pellicle comprising flossing regularly with a monofilament dental tape coated with a permanent abrasive coating and overcoated with a saliva soluble coating suitable for physically removing biofilms, tartar and stained pellicle from interproximal, subgingival and gingival margin areas of teeth.

5. A method for manufacturing monofilament dental tapes coated with a permanent abrasive and overcoated with a saliva soluble coating comprising:

(a) precoating said tape with a permanent adhesive at from between about 1% and about 30% by weight of said monofilament tape (b) adding an abrasive at from between about 0.25% and about 20% by weight of the monofilament tape (c) curing said adhesive/abrasive coating (d) coating said treated tape with a saliva soluble coating at from between about 30 mg/yd and about 70 mg/yd.

6. A dental floss or tape having a permanent coating of abrasive thereon overcoated with a saliva soluble coating.

* * * * *